US00PP23941P3

(12) United States Plant Patent
Zwetzig

(10) Patent No.: US PP23,941 P3
(45) Date of Patent: Oct. 1, 2013

(54) *HIBISCUS* PLANT NAMED 'COPPER QUEEN'

(50) Latin Name: *Hibiscus moscheutos×H. coccineus*
Varietal Denomination: Copper Queen

(75) Inventor: Gretchen Zwetzig, Lindsay, CA (US)

(73) Assignee: Gretchen Zwetzig, Lindsay, CA (US)

( * ) Notice: Subject to any disclaimer, the term of this patent is extended or adjusted under 35 U.S.C. 154(b) by 116 days.

(21) Appl. No.: 12/932,350

(22) Filed: Feb. 24, 2011

(65) Prior Publication Data

US 2012/0222176 P1 Aug. 30, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — June Hwu

(57) ABSTRACT

A new and distinct cultivar of winter hardy *Hibiscus* plant named 'Copper Queen' is the result of a unique hybridization. This new and distinct cultivar is characterized primarily as to its novelty by its extreme cold hardiness to Zone 4, its large thick-textured and heavily streaked flowers of red, pink and white and its ovate to "Maple-shaped" foliage with its reddish-purple coloration, compactness of approximately 2½ feet, its vigorous and uniform breaking habit and its floriferous nature from midsummer until frost.

2 Drawing Sheets

Latin name: *Hibiscus moscheutos×H. coccineus.*
Varietal denomination: 'Copper Queen', hardy *Hibiscus.*

FIELD OF THE INVENTION

This plant, as a hybridized hardy *Hibiscus*, is valuable to the landscape market for its improvements in thicker textured and brightly colored flowers and buds, refined, ovate to "maple-like" foliage with a bronze-purple color, its all-around vigor, stable compact breaking action, and adaptation to extreme environments, including the ability to consistently survive winter temperatures of at least −30 degrees Fahrenheit.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed ovate to "maple-shaped" leaves of a bronze-purple color and relatively smooth margins which combined compliments the landscape;
(b) Medium to large-sized flowers that are outstanding for their red, hot-pink and white colored, heavily streaked petals;
(c) The plant being very floriferous with flowers that stay open for at least one to two days;
(d) The plant being small to medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Copper Queen' was the result of a 50-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 2001 and was selected by Gretchen Zwetzig on Gretchen Zwetzig's property located at 8101 S. 14th St. 68512 Lincoln, Nebr. (previous address for applicants, Fleming's). Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar at 2½ years of age are shown in the attached photographs.

More specifically.

Figure 1:
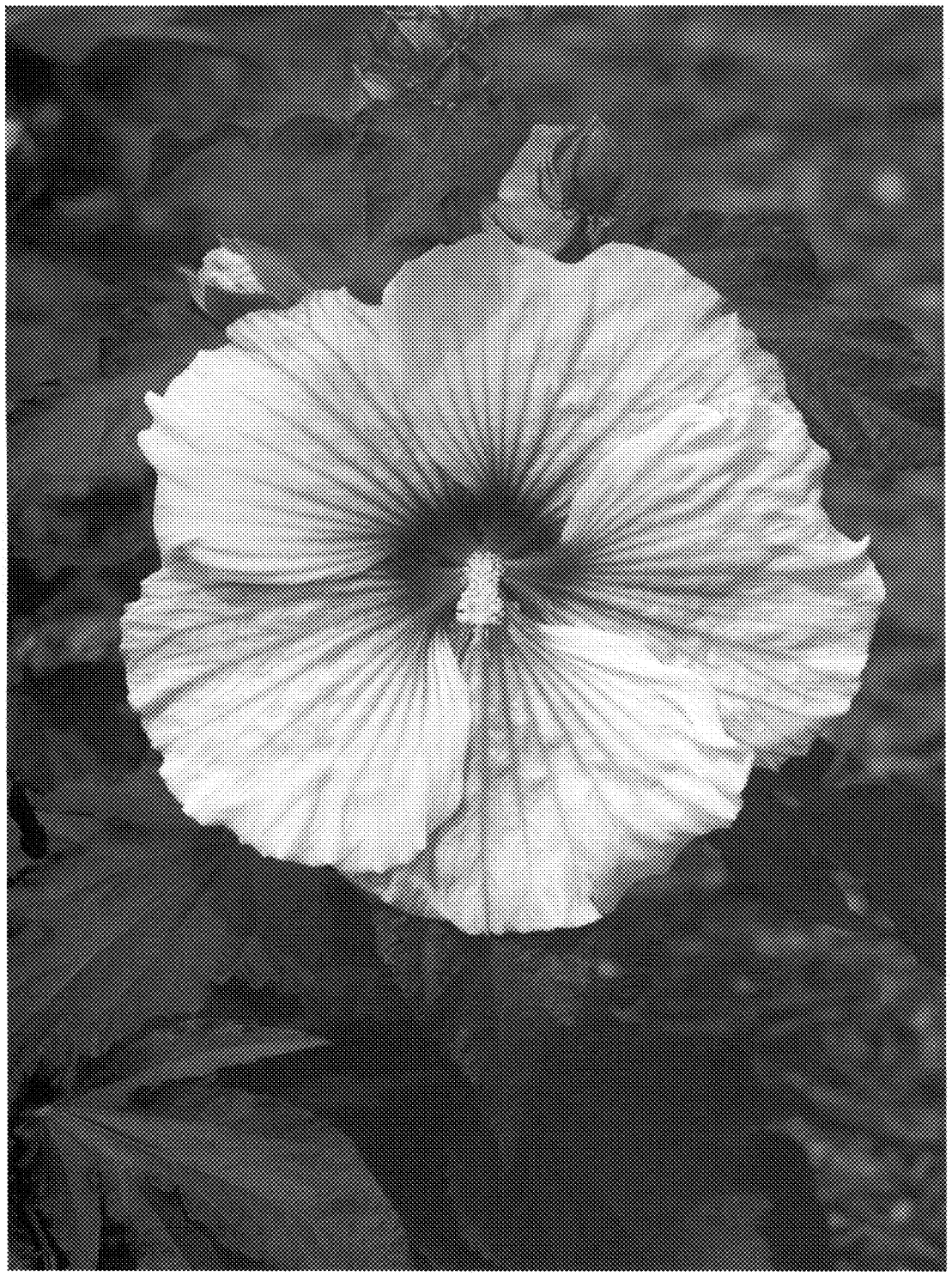
FIG. 1 is a close-up of the flower and the leaf.
Figure 2:
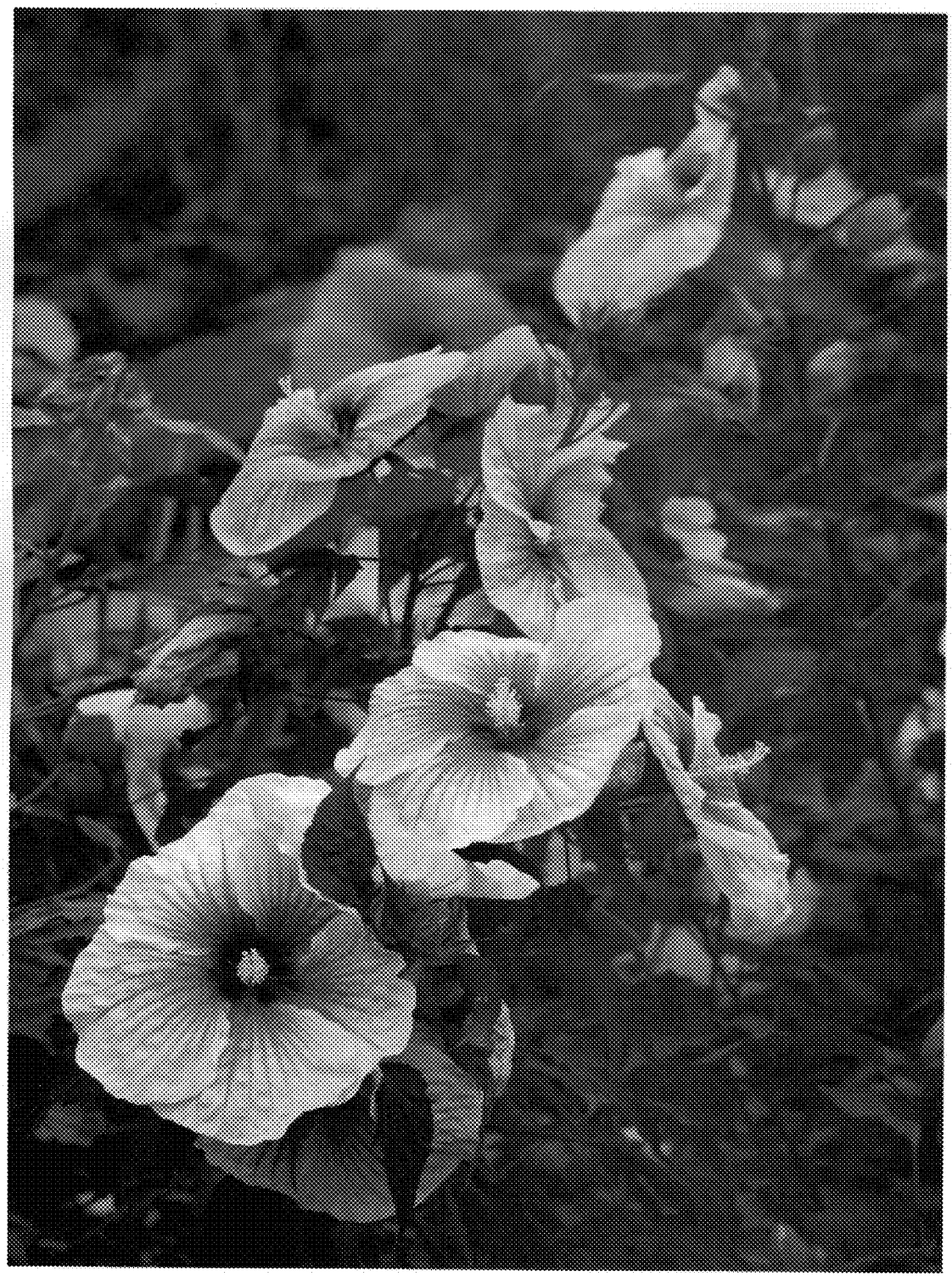
FIG. 2 is a depiction of the whole plant.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart (2001), while general color recitations are consistent with ordinary American terminology.

'Copper Queen' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4) and Lindsay, Calif. (USDA Zone 9).

THE PLANT

Parentage:

*Seed parent.*—*Hibiscus moscheutos*, unnamed and unpatented Fleming-bred seedling.

*Pollen parent.*—*Hibiscus coccineus*, unnamed and unpatented Fleming-bred seedling.

Comparison between Observed Plant and Parents: Parents were similar, except for being approximately ½ foot taller in height than Observed Plant.

Comparison between Observed Plant and other Known Cultivars: The Observed Plant is unique, but most similar to Fleming patented hardy *Hibiscus*: Kopper King U.S. Plant Pat. No. 10,793 and the other patented hardy *Hibiscus* from Fleming's, in that: (a) they are all more compact at 3 feet on average. (b) they are all more hardy to −30 degrees Fahrenheit. (c) they all have refined new leaf shapes and colors. (d) they all have thick, overlapping new flower colors with blooms from the top to the bottom of the plant.

Origin: A selected seedling from stated cross.

Type of plant: Hardy, herbaceous perennial.

Classification: Variety of hardy *Hibiscus* plant.

Propagation: Relatively easy to propagate through cuttings; holds its distinguishing characteristics through successive cuttings and divisions.

Size: About 2½ to 3 feet tall and about 2½ feet wide.

Form: Symmetrical annual growth from perennial roots.

Habit: Upright and uniformly branched.

Growth: Vigorous; medium and compact. Full grown (2½ to 3 ft) in 2 years. 2 ft 6 in at the time of measurement.

Hardiness: Hardy to at least −30 degrees Fahrenheit.

General health: Plant is very disease resistant against rot, aphids, spider mites, scale, white fly etc.; sturdy through excessive drought, rain or wind.

Propagation: Relatively easy and fast rooting in approximately 2 weeks.

Foliage:

1. *Arrangement*.—Alternate.
2. *Shape*.—Juvenile: 3-5 lobed ovate to "maple-shaped" leaves. Rounded base shape. Mature: Refined, ovate to "maple-shaped", 3-5 lobed leaf with entire to mildly serrate margins and acute apices; rounded base.
3. *Size*.—Mature leaf (petiole base to apex): Length is about 5 inches or (12.5 cm), width is about 3 inches or (7.5 cm). Young leaf: Length 3¾ inches or (9.5 cm), width is 2½ inches or (5.7 cm).
4. *Color*.—Young leaves (upper side): 147-A; (purple color): Mainly N 92-A and 187-A. Mature leaves: (upper side): 147-A. Mainly a blend of 187-A and 178-A. Veins: 185-A. Venation pattern: Palmate. Venation Color: 185-A Upper and Lower Surface. Coloration of the lower leaf surface: Between 137 C and 139 C. Mature Leaf.
5. *Surface texture*.—Upper: Smooth. Lower: Semi-smooth.
6. *Petiole length*.—About 2¾ inches or 6.5 cm. Diameter: 1-2 cm.
7. *Petiole color*.—137-A and 178-A. Surface Texture: Semi-smooth.

Stems: The stems are stout at the base becoming more slender toward the apices; coloration is consistent with the petiole.

Length: 2-3 inches. Diameter: 1-2 cm.

Internode length: Apx. 2 inches.

Texture: Semi-smooth.

THE FLOWER

Blooming period: Profuse from July until frost.

Flower diameter: Large; about 9-10 inches (24 cm).

Borne: Singly in leaf axils, from midpoint of stems upward.

Bloom duration: Individual bloom lasts at least one to two full days.

Form: Campanulate; petals are also very overlapping.

Average number of flowers per season: 300.

Bud:

1. *Length*.—About 2¼ inches or (6 cm) on day before opening. Diameter: apx. 2 inches.
2. *Color*.—Between 49-D and 46-C (edges).
3. *Surface texture*.—Semi-glabrous.
4. *Duration*.—One to two weeks.

Corolla: Having five petals.

1. *Petal character and dimensions*.—Campanulate and very overlapping. (a) Young Length: About 3¾ inches or (9.5 cm). Mature Length: About 5 inches or (13 cm). (b) Young Width: About 2½ inches or (5.7 cm). Mature Width: About 3 inches or (8 cm).
2. *Coloration*.—Red, hot-pink and white. Red: 53-A, 45-A and 187-A. Pink: 50-A and 50-C. White: 56-D. (a) Streaks and venation: 53-A, 50-A and 50-C. White background coloration of petal surface: Closest to 56-D. (b) "Kissed" speckled petal edge: 53-A and 50-A. (c) Eye zone: 53-A, 45-A and 187-A. Size:2 ½ inches or (6½ cm).
3. *Texture*.—Smooth.
4. *Substance*.—Thick.
5. *Shape*.—Campanulate and very overlapping with petal folds at edges.

Reproductive organs:

1. *Staminal column*.—Stamen along basal two-thirds. One stamen per flower. Stamen average length: About 1¾ inches or (4.8 cm). Filament length: 1¼" (3.17 cm). Stamen color designation: Lighter than 11-D. Pollen color: 11-C and B.
2. *Style*.—Terminates upper one-third of stamina column. Average length: ½", 1.27 cm. Stigmatic lobe and Style color: 11-D (tips: 63-A). Stigma size: ¼".

Calyx: Average of one per plant: 5 lobed, connate at the base; about 1¼ inches or (3.5 cm) in length. Upper and Lower Color: Medium green: 147-A. Surface texture: Semi-smooth.

Stipules: None.

Seed (fruit): Size: 1 cm. Color: Grey-brown. Average number: Less than 100.

Epicalyx: Whorl of bracts.

1. *Shape.*—10-12 slender, sword-shaped bractlets.
2. *Length.*—About 1½ inches or (3.8 cm).
3. *Upper and lower color.*—143-A.

Penduncle:

1. *Length.*—About 2 inches or (6½ cm). Diameter: 1 cm.
2. *Strength.*—Stiff and sturdy. Surface Texture: Semi-smooth.
3. *Color.*—Light to medium green with slight reddish-purple cast. 148-A and 175 A.

The invention claimed is:

1. A new and distinct cultivar of hardy *Hibiscus* plant, as herein shown and described, characterized by its compact nature, refined ovate to "maple-shaped" foliage of a bronze-purple coloration, its large heavily streaked, red, hot-pink and white flowers, its vigor and its hardiness.

* * * * *